United States Patent
Matsumoto et al.

(10) Patent No.: US 6,982,336 B2
(45) Date of Patent: Jan. 3, 2006

(54) 1,2-DIOXETANE DERIVATIVES, LUMINESCENT REAGENTS, LUMINESCENCE METHODS AND MEASURING METHODS

(75) Inventors: Masakatsu Matsumoto, Machida (JP); Nobuko Watanabe, Kamakura (JP); Masashi Yamada, Yokohama (JP)

(73) Assignee: Tosoh Corporation, Shinnanyo (JP)

( * ) Notice: Subject to any disclaimer, the term of this patent is extended or adjusted under 35 U.S.C. 154(b) by 702 days.

(21) Appl. No.: 10/091,447

(22) Filed: Mar. 7, 2002

(65) Prior Publication Data

US 2002/0132365 A1    Sep. 19, 2002

(30) Foreign Application Priority Data

Mar. 8, 2001    (JP)    ............ 2001-065347

(51) Int. Cl.
- G01N 21/76    (2006.01)
- C07D 261/08    (2006.01)
- C07D 275/02    (2006.01)
- C07D 417/14    (2006.01)
- C07F 7/18    (2006.01)

(52) U.S. Cl. .......... 548/247; 422/52; 436/93; 436/172; 436/546; 514/372; 514/378; 548/110; 548/119; 548/214; 549/50; 549/464; 549/510

(58) Field of Classification Search ........... 548/247, 548/214, 110, 119; 549/510, 50, 464; 436/172, 436/372, 378, 93, 546; 422/52; 514/372, 514/378

See application file for complete search history.

(56) References Cited

U.S. PATENT DOCUMENTS

| | | | |
|---|---|---|---|
| 5,616,729 A * | 4/1997 | Schaap et al. | 549/223 |
| 5,650,525 A * | 7/1997 | Matsumoto | 549/510 |
| 5,698,727 A * | 12/1997 | Matsumoto | 556/470 |
| 5,731,445 A | 3/1998 | Matsumoto et al. | |
| 5,770,743 A * | 6/1998 | Schaap et al. | 548/526 |
| 5,856,522 A * | 1/1999 | Bronstein et al. | 549/218 |
| 5,877,333 A | 3/1999 | Matsumoto et al. | |
| 5,929,254 A * | 7/1999 | Matsumoto | 549/214 |
| 6,218,135 B1 | 4/2001 | Matsumoto et al. | |
| 6,228,653 B1 | 5/2001 | Matsumoto et al. | |
| 6,660,529 B2 * | 12/2003 | Edwards et al. | 436/172 |
| 6,747,160 B2 * | 6/2004 | Matsumoto et al. | 548/526 |
| 6,844,453 B2 * | 1/2005 | Matsumoto et al. | 549/510 |

FOREIGN PATENT DOCUMENTS

| | | |
|---|---|---|
| EP | 0 401 001 | 12/1990 |
| EP | 0 943 618 | 9/1999 |

OTHER PUBLICATIONS

Matsumoto, M., et al., "Synthesis of bicyclic dioxetanes bearing a 3-hydroxy-4-isoxazolylphenyl moiety," Tetrahedron Letters, vol. 43(49), pp. 8955-8958 (Dec. 2002), at p. 8955, col. 2, lines 7-11 and Fig.1, compound 3a; and p. 8956, Table 1.*

Beck, S. and Koster, H., "Applications of Dioxetane Chemiluminescent Probes to Molecular Biology," Analytical Chem., vol. 62(21), pp. 2258-2270 (Nov. 1990), at p. 2261, col. 1, lines 15-21 and 31-32; p. 2261, col. 2, lines 38 et seq. (Fig. 6).*

Adam, W., et al., "Hydrogen-Bonding Effects on the Fluorescence versus Electron-Transfer-initiated Chemiluminescence Spectra of the m-Oxybenzoate Ion Derived from a Bicyclic Dioxetane," J. Org. Chem., vol. 65(7), pp. 2078-2082 (Apr. 2000) at p. 2079.*

Adam, W., et al., "Solvatochromic Effects on the Electron Exchange Chemiluminescence (CIEEL) of Spiroadamantyl-Substituted Dioxetanes and the Fluorescence of Relevant Oxyanions," J. Phys. Chem. A, vol. 102(28), pp. 5406-5414 (Jul. 1998), at p. 5407, Sch.1.*

Matsumoto, M., "Design and synthesis of chemiluminescent substrates with high luminescent efficiency in an aqueous system," Luminescence, vol. 16, pp. 275-280 (Jul.-Aug. 2001), at p. 279, col. 2, lines 12-37 & Table 1; p. 280, lines 3-12.*

Matsumoto, M., et al., "Synthesis and chemiluminescent decomposition of spiro[1,2-dioxetane-3,6'-benzo(c)chromene]s," Luminescence, vol. 14, pp. 341-344 (Nov.-Dec. 1999), at p. 341, col. 1, lines 3-12; p. 344, col. 1, lines 8-16.*

M. Matsumoto, et al.: "Synthesis and Chemiluminescence of 3-Biphenyl-4,4-Diisopropyl-3-Methoxy-1,2-Dioxetanes", Heterocycles, vol. 41, No. 11, Nov. 1, 1995, pp. 2419-2422.

U.S. Appl. No. 10/382,853, filed Mar. 7, 2003, Matsumoto et al.

U.S. Appl. No. 10/091,447, filed Mar. 7, 2002, Matsumoto et al.

U.S. Appl. No. 10/798,338, filed Mar. 12, 2004, Matsumoto et al.

* cited by examiner

Primary Examiner—Kamal A. Saeed
Assistant Examiner—Anthony J. Paviglianiti
(74) Attorney, Agent, or Firm—Oblon, Spivak, McClelland, Maier & Neustadt, P.C.

(57) ABSTRACT

A 1,2-dioxetane derivative of the formula (I):

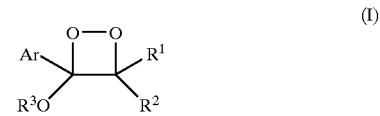

wherein $R^1$–$R^3$ and Ar are defined in the claims is provided.

10 Claims, No Drawings

1,2-DIOXETANE DERIVATIVES, LUMINESCENT REAGENTS, LUMINESCENCE METHODS AND MEASURING METHODS

The present invention relates to 1,2-dioxetane derivatives. The 1,2-dioxetane derivatives of the present invention are compounds which are capable of inducing chemiluminescence and can be used, for example, as substrates for immunoassay.

Heretofore, various 1,2-dioxetane derivatives have been synthesized, and it is known that compounds having a spiroadamantyl group bonded at the 3-position, are useful as chemiluminescent substrates (see, for example, JP-B-5-21918, and JP-B-5-45590). Further, as produced by the present inventors, compounds disclosed in JP-A-8-245615, JP-A-8-169885 and JP-A-8-165287, are known. However, these 1,2-dioxetane derivatives were poor in thermal stability. JP-A-9-216887 discloses compounds having the thermal stability improved.

As mentioned above, various studies have been made with respect to 1,2-dioxetane derivatives, and various compounds have been produced. However, for such compounds to be useful in the field of e.g. clinical tests, the compounds themselves are required to be stable and easy to handle and capable of emitting light at high efficiency. Accordingly, it has been desired to develop a compound superior to conventional compounds.

Conventional compounds including the compounds disclosed in the above-mentioned JP-A-9-216887, were poor in luminous efficiency in a protic solvent of e.g. an aqueous type, and even if they were employed for an immunoassay in a practical clinical test, they were unable to provide practically sufficient strength, if a protic solvent is used as a measuring condition. Accordingly, at the time of measurement, a substance which enhances luminescence, other than the 1,2-dioxetane derivatives, was required to be present as an enhancer.

As enhancers, cationic surfactants (such as cetyltrimethylammonium bromide and cetyldimethylbenzylammonium chloride), water-soluble polymerized quaternary onium salts, (including quaternary ammonium salts, quaternary sulfonium salts and quaternary phosphonium salts, such as poly(vinylbenzyldimethylbenzylammonium chloride), poly(vinylbenzyltrimethylammonium chloride) and poly(vinylbenzyltributylammonium chloride)), natural polymers (such as serum albumin, immunoglobulin and serum lipoprotein of mammals), etc., were used. However, when these enhancers were used, the viscosity tended to be high, whereby a due care was required in handling. Accordingly, if there is a compound which is capable of showing high luminous efficiency without using any enhancer even in a protic solvent, such a compound is more useful.

Under these circumstances, the present inventors have conducted an extensive study to develop a compound which is superior to conventional compounds and as a result, have found that a 1,2-dioxetane derivative having an aromatic ring substituent having a 5-membered hetero ring such as an isoxazole ring of the following formula (A) or (B) bonded thereto, exhibits high luminous efficiency even without using any enhancer even in a protic solvent such as water. The present invention has been accomplished on the basis of this discovery.

Namely, the present invention provides a 1,2-dioxetane derivative of the formula (I):

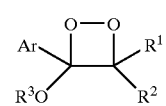

(I)

wherein each of $R^1$ and $R^2$ which are independent of each other, is a hydrogen atom, an alkyl group or an aryl group, or $R^1$ and $R^2$ may together form a cyclic or polycyclic organic ring group spiro-bonded to the dioxetane ring, $R^3$ is an alkyl group or an aryl group, or $R^3$ and $R^1$ or $R^2$ may together form a condensed ring containing the dioxetane ring and a hetero atom, and Ar is a group of the formula (A):

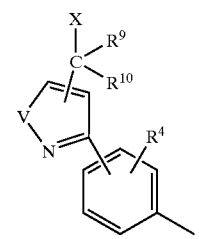

(A)

wherein $R^4$ is a hydroxyl group, an alkoxyl group, an aralkyloxy group, a group of —$OSi(R^5R^6R^7)$ (wherein each of $R^5$, $R^6$ and $R^7$ which are independent of one another, is an alkyl group or an aryl group), a phosphate group or a group of —$S(C=O)R^8$ (wherein $R^8$ is an alkyl group or an aryl group), each of $R^9$ and $R^{10}$ which are independent of each other, is a hydrogen atom, an alkyl group, an aryl group or a halogen atom, X is a halogen atom, and V is an oxygen atom or a sulfur atom, or a group of the formula (B):

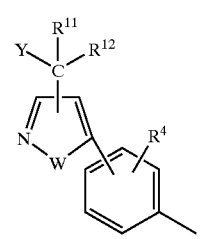

(B)

wherein $R^4$ is the same as $R^4$ in the above formula (A), each of $R^{11}$ and $R^{12}$ which are independent of each other, is a hydrogen atom, an alkyl group, an aryl group or a halogen atom, Y is a halogen atom, and W is an oxygen atom or a sulfur atom.

Further, the present invention provides a chemiluminescent reagent which contains the above 1,2-dioxetane derivative. Further, the present invention provides a luminescence method which comprises decomposing the above 1,2-dioxetane derivative to have chemiluminescence generated. Still further, the present invention provides a measuring method which comprises measuring a substance to be detected, in a test sample, by means of the above luminescence method. Furthermore, the present invention provides a luminescence method which comprises letting a compound having a 1,2-dioxetane structure emit light in a protic solvent in the absence of any other enhancer.

Now, the present invention will be described in further detail with reference to the preferred embodiments.

In this specification, "an alkyl group" means a $C_{1-20}$ straight chain, branched or cyclic alkyl group which may have a substituent, and the alkyl group is a straight chain group such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl or icosanyl, a group in which such an alkyl group is branched, or a group in which such an alkyl group is cyclic. The substituent which such an alkyl group may have, is, for example, a hydroxyl group, an alkoxyl group or an aryl group. The alkoxyl group may, for example, be one having from 1 to 5 $C_{1-20}$ alkoxyl groups bonded in a straight chain form or in a branched form, such as methoxy, ethoxy, propoxy, butoxy, pentyloxy, hexyloxy, methoxyethoxy, methoxypropoxy, ethoxyethoxy, ethoxypropoxy or methoxyethoxyethoxy. Further, the above aryl group may, for example, be a $C_{6-20}$ aromatic hydrocarbon group such as phenyl or naphthyl, or a heteroaryl group having from 1 to 5 nitrogen atoms, oxygen atoms or sulfur atoms in a ring, such as furyl, thienyl or pyridyl.

Further, in this specification, "an alkoxyl group" may be the same as the alkoxyl group which may be substituted on the above alkyl group, and "an aryl group" may be the same as the aryl group which may be substituted on the above alkyl group. Further, in this specification, "a polycyclic organic ring group" is a $C_{6-30}$ polycyclic alkylene which may optionally be substituted from 1 to 10 groups independently selected from $C_{1-10}$ alkyl, $C_{1-10}$ alkoxyl, halogen and halo-$C_{1-10}$ alkyl, such as an adamantyl group or a bicyclo[2.2.1]heptyl group. Further, a halogen atom, an alkyl group, an aryl group, a cyano group, an amide group, an alkoxyl group, or a carboxyl group may be bonded to optional carbon of the polycyclic organic ring group. Further, "an aralkyloxy group" is a $C_{7-20}$ group such as benzyloxy or phenethyloxy, and "a halogen atom" may, for example, be fluorine, chlorine or bromine.

Further, the case wherein in the formula (I), $R^3$ and $R^1$ or $R^2$ together form a condensed ring containing the dioxetane ring and a hetero atom, may, for example, be a condensed ring of the dioxetane ring and a furan ring, or a condensed ring of the dioxetane ring and a pyran ring.

In the present invention, preferred is one wherein in the above formula (I), wherein Ar is a group of the formula (a):

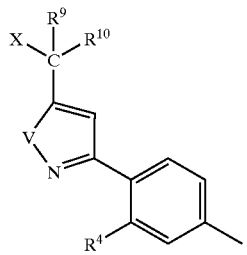

(a)

wherein $R^4$, $R^9$, $R^{10}$, X and V are the same as $R^4$, $R^9$, $R^{10}$, X and V in the above formula (A), or a group of the formula (b):

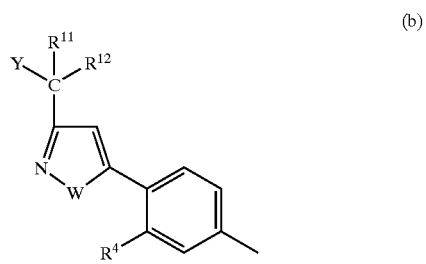

(b)

wherein $R^4$, $R^{11}$, $R^{12}$, Y and W are the same as $R^4$, $R^{11}$, $R^{12}$, Y and W in the above formula (B).

It is preferred that in the formula (I), $R^3$ and $R^1$ or $R^2$ together form a condensed ring of a dioxetane ring and a furan ring, and more preferably, $R^2$ or $R^1$ which does not form the condensed ring together with $R^3$, is a $C_{3-4}$ alkyl group. Particularly preferred is a compound represented by the formula (I'):

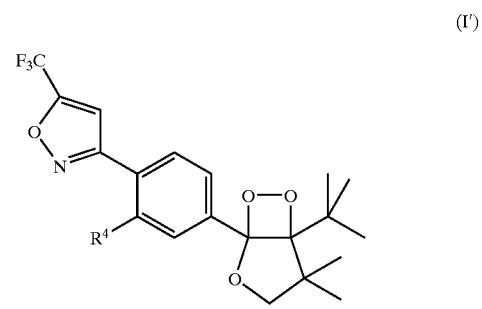

(I')

wherein $R^4$ is as defined above.

The 1,2-dioxetane derivative of the formula (I) of the present invention can be produced in accordance with the following reaction scheme from an enol ether derivative of the formula (II):

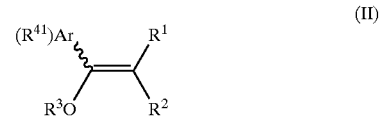

(II)

wherein $R^1$ to $R^3$ are the same as $R^1$ to $R^3$ in the formula (I), $R^{41}$ is an alkoxyl group or an aralkyloxy group, and $(R^{41})$Ar is an aryl group substituted by $R^{41}$, represented by a group of the formula (A'):

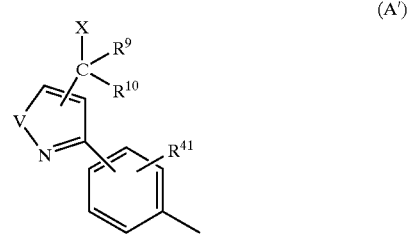

(A')

wherein $R^9$, $R^{10}$, X and V are the same as $R^9$, $R^{10}$, X and V in the above formula (A), and $R^{41}$ is the same as $R^{41}$ in the above formula (II) or a group of the formula (B'):

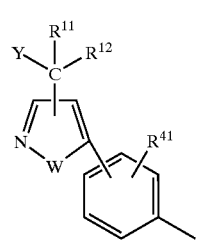

(B')

wherein $R^{11}$, $R^{12}$, Y and W are the same as $R^{11}$, $R^{12}$, Y and W in the above formula (B), and $R^{41}$ is the same as $R^{41}$ in the above formula (II).

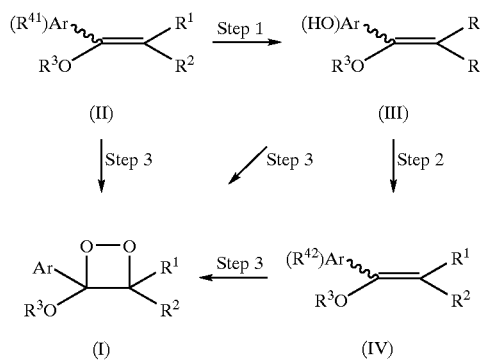

In the above formulae, $R^1$ to $R^3$ and $R^{41}$ are the same as $R^1$ to $R^3$ and $R^{41}$ in the above formulae (I) and (II), and $R^{42}$ is a group of the formula —OSi($R^5R^6R^7$) (wherein $R^5$, $R^6$ and $R^7$ are the same defined above) or a group of the formula:

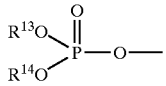

(wherein each of $R^{13}$ and $R^{14}$ is an alkali metal, a quaternary ammonium salt or an alkyl group, or $R^{13}$ and $R^{14}$ may together form a ring). The group of (HO)Ar in the compound of the formula (III) is one having an OH group at the same position as the position of substituent $R^{41}$ in the formula (II), and ($R^{42}$)Ar in the formula (IV) is one having a substituent $R^{42}$ at the same position as the position of the substituent $R^{41}$ in the formula (II).

Step 1: In this step, a compound of the formula (II) is subjected to a protective group-removing reaction to produce a compound of the formula (III). The compound which is subjected to the protective group-removing reaction is a compound of the above formula (II), wherein $R^1$ to $R^3$ are as defined above, and $R^{41}$ is a protective group for a hydroxyl group (preferably a methoxy group or a benzyloxy group). Such a reaction can be carried out by a method well known to those skilled in the art, i.e. by reacting it with an anion of an alkylthiol, or by subjecting it to a hydrogenation reaction. Either reaction may be selected for use depending upon the group to be removed.

Step 2: In this step, in order to form a silyloxy group or a phosphoric acid group, the corresponding halogenated trialkoxysilane or halogenated phosphate is reacted to the compound of the above formula (III) to produce a compound of the formula (IV). In this step, for example, if chloroethylene phosphate is reacted in order to introduce a phosphoric acid group, the product can be converted by sodium cyanide to a sodium salt of cyanoethyl phosphate, and the cyanoethyl group is further removed, followed by conversion to an ammonium sodium salt. This ammonium sodium salt can easily be converted to a disodium salt, for example, by a reaction with sodium hydrogencarbonate.

Step 3: In this step, the compound of the formula (II), (III) or (IV) is reacted with singlet oxygen to produce a 1,2-dioxetane derivative of the formula (I). The reaction with singlet oxygen can be accomplished by subjecting the enol ether derivative of the above formula (II), (III) or (IV) to visible light irradiation in an oxygen atmosphere in the co-existence of a photosensitizer such as Methylene Blue, Rose Bengale or tetraphenylporphine (TPP). Here, as a solvent, a halogenated hydrocarbon such as dichloromethane, dichloroethane or carbon tetrachloride, or an alcohol such as methanol or ethanol, may be employed. Further, the reaction is preferably carried out at a temperature of from −80° C. to room temperature.

The following method may, for example, be mentioned as a method for producing the enol ether derivative of the above formula (II).

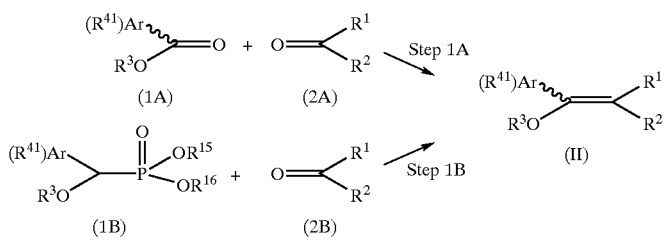

In the above formulae, $R^1$ to $R^3$ and $R^{41}$ are the same as $R^1$ to $R^3$ and $R^{41}$ in the above formulae (I) and (II). Each of $R^{15}$ and $R^{16}$ is an alkyl group, or $R^{15}$ and $R^{16}$ may together form a ring.

Step 1A: In this step, an aromatic carboxylic acid ester of the formula (1A) is reacted with a ketone of the formula (2A) to produce an enol ether derivative of the formula (II). The reaction is carried out in the presence of titanium, as an essential requirement. It is usually preferred that titanium is formed into a reduced state by treating titanium halide such as titanium chloride with a reducing agent such as lithium aluminum hydride and a base such as triethylamine, and then used for the reaction. The reaction may be carried out in an organic ether such as tetrahydrofuran (THF). The reaction may proceed at a temperature of from 0 to 100° C., but the reaction is preferably carried out under reflux of THF, from the viewpoint of the operation efficiency and reactivity.

Step 1B: In this step, an arylmethylphosphonate of the formula (1B) is reacted with a ketone of the above formula (2B) to produce an enol ether derivative of the above formula (II).

The arylmethylphosphonate of the above formula (1B) is a compound which can easily be produced by the method disclosed in the above-mentioned JP-B-5-45590. It is preferred that diisopropylamine is treated with butyl lithium or the like to form a lithium amide, which is used for the reaction. The reaction can be carried out in an organic ether such as tetrahydrofuran (THF). The reaction is preferably carried out at a temperature of from −78° C. to room temperature.

In a case where the compound of the above formula (II) is a dihydrofuran derivative, the following method may, for example, be mentioned as the method for its production.

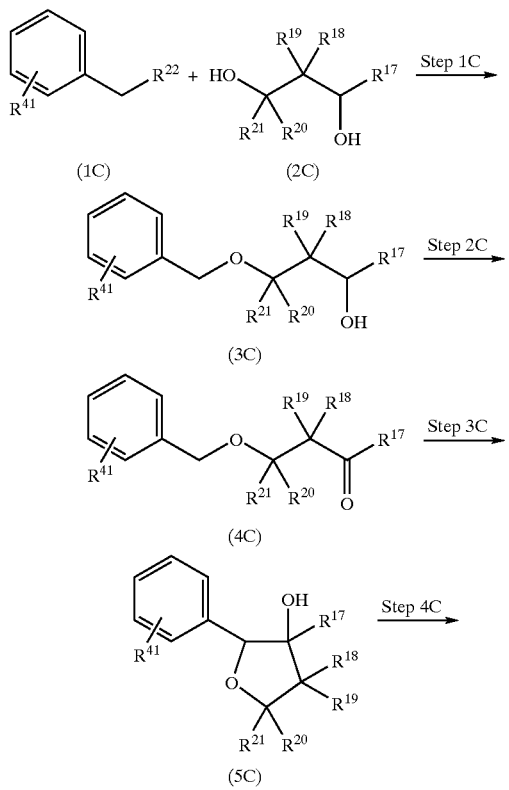

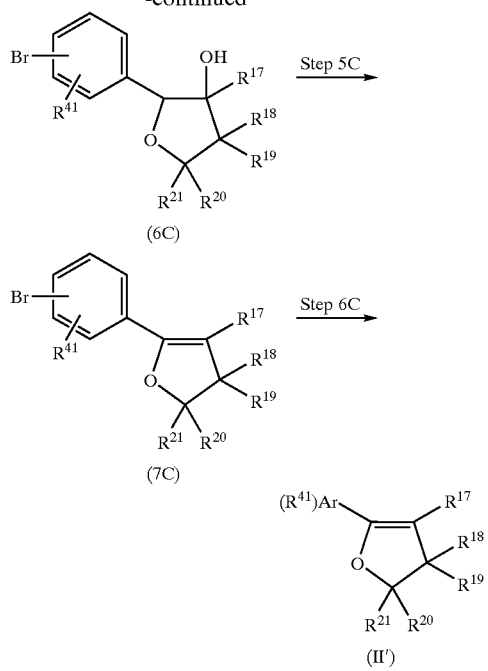

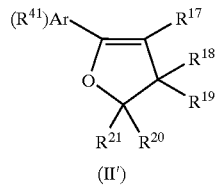

In the above formulae, each of $R^{17}$, $R^{18}$, $R^{19}$, $R^{20}$ and $R^{21}$ which are independent of one another, is a hydrogen atom, an alkyl group or an aryl group. Further, each pair of $R^{18}$ and $R^{19}$, $R^{20}$ and $R^{21}$, $R^{17}$ and $R^{19}$, $R^{17}$ and $R^{20}$, and $R^{18}$ and $R^{20}$, which are independent of one another, may form a cyclic alkyl group. $R^{41}$ is as defined above. $R^{22}$ is a halogen atom, a substituted sulfonyloxy group or a hydroxyl group.

Step 1C: In this step, a compound of the above formula (1C) is reacted with a compound of the above formula (2C) to produce a compound of the above formula (3C). The reaction can be accomplished by a so-called Williamson synthesis. Here, in a case where substituent $R^{22}$ of the compound of the formula (1C) is a halogen atom or a substituted sulfonyloxy group, such a compound can be subjected directly to the reaction, and in a case where $R^{22}$ is a hydroxyl group, such a group is converted to a sulfonyloxy group by e.g. tosyl halide in the reaction system, and then the compound is subjected to the reaction, to accomplish this step.

Step 2C: In this step, the compound of the above formula (3C) is oxidized to produce a compound of the above formula (4C). The oxidation in this step can be carried out by means of a chromium type oxidizing agent or an activating agent. As the chromium type oxidizing agent, pyridinium chlorochromate (PCC) or pyridinium dichlorochromate (PDC) may, for example, be used. At that time, a halogenated hydrocarbon such as dichloromethane may be used as the solvent. Further, in a case where the above-mentioned activating agent is employed, the reaction can be carried out by a combination with a solvent, such as a $Py.SO_3$/triethylamine/DMSO, $Ac_2O$/DMSO system.

Step 3C: In this step, the compound of the above formula (4C) is subjected to ring closure to produce a compound of the above formula (5C). The reaction is carried out by using a lithium salt of a secondary amine such as lithium diisopropylamide, or a base such as t-butoxypotassium. As the solvent, an organic solvent such as THF or DMSO, may be employed. The reaction is preferably carried out at a temperature of from 0° C. to room temperature for from 1 to 5 hours.

Step 4C: In this step, the compound of the above formula (5C) is brominated to produce a compound of the above formula (6C). The reaction is carried out by using a brominating agent such as N-bromosuccinimide. As the solvent, an organic solvent such as water-containing THF, dioxane or DMF, may be used.

Step 5C: In this step, the compound of the above formula (6C) is dehydrated to produce a compound of the above formula (7C). The reaction is carried out by reacting thionyl chloride in the presence of a base such as pyridine, or by using as a catalyst an acid such as phosphoric acid or p-toluenesulfonic acid. As the solvent, a halogenated hydrocarbon such as methylene chloride, or an aromatic hydrocarbon such as toluene, may be employed, and the solvent may suitably be selected for use depending upon the reagent to be reacted.

Step 6C: In this step, from the compound of the above formula (7C), a compound of the above formula (II') is produced. The reaction is such that the bromine of the compound of the above formula (7C) is substituted to introduce the desired substituent to produce the compound of the above formula (II'). A substituted amino group may be introduced in such a manner that a carboxyl group is introduced by means of a lithium salt such as butyl lithium, followed by reaction with an amine or ammonia by using carbonylimidazole as a condensing agent. Further, from the amide produced by the above reaction, for example, a compound having an oxazoline ring may be obtained by reacting substituted or unsubstituted ethanolamine. Further, an acyl group may be introduced in such a manner that a lithium salt such as butyl lithium is employed in the same manner as above and is reacted with N-methylformanilide or with an aldehyde such as acetaldehyde or benzaldehyde, followed by oxidizing the hydroxyl β group by an oxidizing agent such as manganese dioxide. Here, the compound having an acyl group is subjected to conversion of the acyl group to a hydroxyimino group, and such a dianion is reacted with a corresponding amide or ester, followed by dehydration to form an isoxazole ring. As an another method, the compound having an acyl group introduced is subjected to conversion to a β-diketone type substituent, and a hydroxylamine is reacted thereto to form an isoxazole ring.

In a case where the compound of the above formula (II) is a dihydropyran derivative, the following method, may, for example, be mentioned as the method for its production.

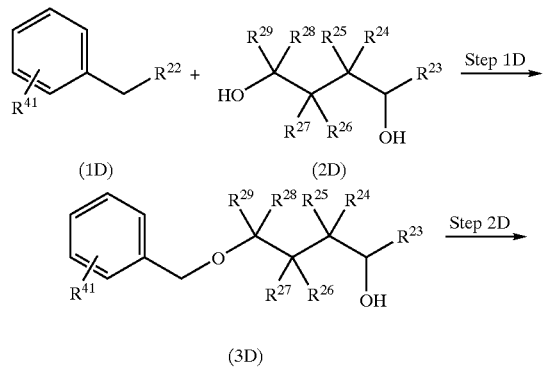

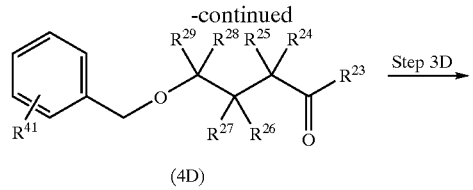
(4D)

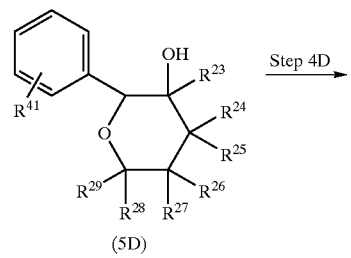
(5D)

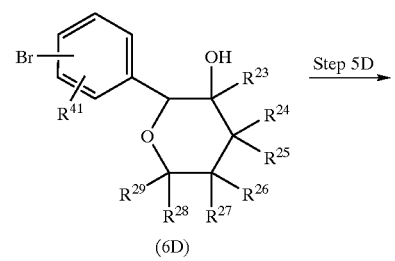
(6D)

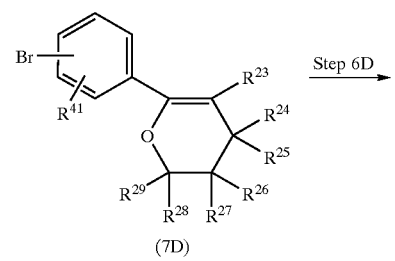
(7D)

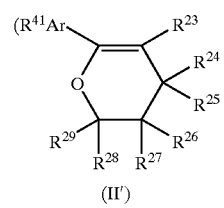
(II')

In the above formulae, each of $R^{23}$, $R^{24}$, $R^{25}$, $R^{26}$, $R^{27}$, $R^{28}$ and $R^{29}$ which are independent of one another, is a hydrogen atom, an alkyl group or an aryl group. Further, each pair of $R^{24}$ and $R^{25}$, $R^{26}$ and $R^{27}$, $R^{28}$ and $R^{29}$, $R^{23}$ and $R^{24}$, $R^{23}$ and $R^{26}$, $R^{23}$ and $R^{28}$, $R^{24}$ and $R^{26}$, $R^{24}$ and $R^{28}$, and $R^{26}$ and $R^{28}$, which are independent of one another, may together form a cyclic alkyl group. $R^{41}$ and $R^{22}$ are as defined above.

Steps 1D, 2D, 3D, 4D, 5D and 6D: The process for producing the compound of the above formula (7D) can be accomplished in the same manner as the above Steps 1C, 2C, 3C, 4C, 5C and 6C.

The 1,2-dioxetane derivative of the formula (I) of the present invention is decomposed into a carbonyl compound in an alkaline condition accompanying chemiluminescence, and it will be decomposed also by an esterase (a carboxylate hydrolase) such as an aryl esterase or acetylcholine esterase, an enzyme such as an alkaline phosphatase, a fluoro compound such as tetrabutylammonium fluoride, or an acidic or amine compound, accompanying chemiluminescence.

Accordingly, the 1,2-dioxetane derivative of the formula (I) can be a chemiluminescent reagent. The decomposition of the 1,2-dioxetane derivative accompanying such chemiluminescence, may be carried out in the presence of other enhancer, or may be carried out in the absence of any other enhancer. It is one of characteristics that the 1,2-dioxetane derivative of the formula (I) exhibits high luminous quantum yield even if the decomposition accompanying chemiluminescence is carried out in a protic solvent and in the absence of any other enhancer. The luminous quantum yield is preferably at least 1%, more preferably at least 10%, particularly preferably at least 20%.

Further, the chemiluminescent reagent of the present invention can be used for all measuring methods intended to obtain the concentrations of substances to be detected in test samples. For example, it can be used as a reagent for measuring immunity in an immunoassay, and further, it can be used also in an enzyme detecting method, a chemical detecting method, a nucleotide probe method.

Substances to be detected in the above immunoassay include, for example, hormones such as hCG, TSH and LH, cancer-related substances such as AFP and CEA, viral antigens and antibodies such as HIV and HTLV-I, and nucleic acids (DNA, RNA).

The above immunoassay can be carried out by a step of preliminarily bonding the above enzyme to a substance having a specific affinity to the substance to be detected as mentioned above, and mixing it with a test sample containing the substance to be detected, reacting the mixture for a predetermined period of time and bonding the substance to be detected in the test sample to the substance having the affinity thereto, and a step of determining the amount of the substance having the affinity, bonded or not bonded. The above step of determining the amount of the substance having the affinity, bonded or not bonded, is carried out in such a manner that the enzyme and the 1,2-dioxetane derivative of the present invention are reacted, whereby the luminescence intensity from the 1,2-dioxetane derivative increases in proportion to the amount of the enzyme, whereby the concentration of the substance can be obtained by measuring the luminescence intensity.

The reagent for immunoassay containing the 1,2-dioxetane derivative of the present invention, and the above-mentioned immunoassay employing it, are also included in the present invention.

The 1,2-dioxetane derivative of the formula (I) of the present invention is capable of exhibiting stable luminous efficiency with high quantum yield and is a stable compound having high thermal stability, whereby depending upon the cold storage, it is stable to such an extent that no decomposition product is observed upon expiration of one year. Accordingly, measurement of luminescence can be carried out simply and efficiently, and it is useful, for example, in the field of clinical tests.

Now, the present invention will be described in further detail with reference to Examples and Reference Examples. However, it should be understood that the present invention is by no means restricted to such Examples.

REFERENCE EXAMPLE 1

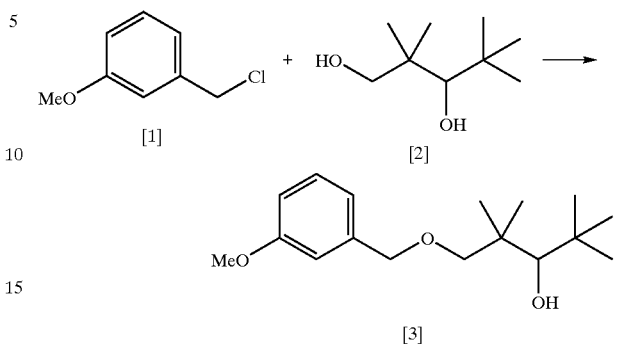

In a nitrogen atmosphere, to a solution having 2.12 g (53.0 mmol) of 60% sodium hydride suspended in 80 ml of DMF at 0° C., 7.05 g (44.1 mmol) of 2,2,4,4-tetramethyl-1,3-pentanediol (compound (2)) dissolved in 15 ml of DMF, was dropwise added over a period of 30 minutes, followed by further stirring for 30 minutes. To this solution, 9.07 g (57.9 mmol) of 3-methoxybenzyl chloride (compound (1)) dissolved in 15 ml of DMF was dropwise added over a period of 30 minutes, followed by stirring for 12 hours. The reaction mixture was put into an aqueous saturated ammonium chloride solution and extracted with ethyl acetate. The extract layer was washed with a saturated sodium chloride aqueous solution, dried over anhydrous magnesium sulfate and then concentrated. The concentrated product was subjected to a silica gel column and eluted with a 10:1 mixed solvent of hexane and ethyl acetate, to obtain 10.7 g of 1-(3-methoxybenzyloxy)-2,2,4,4-tetramethyl-3-pentanol (compound (3)) in a yield of 86.7% as a colorless oily substance.

$^1$HNMR (400 MHz, CDCl$_3$); δ 1.03 (s, 9H), 1.04 (s, 3H), 1.07 (s, 3H), 3.23 (d, J=4.9 Hz, 1H), 3.25 (d, J=8.8 Hz, 1H), 3.41 (d, J=8.8 Hz, 1H), 3.43 (d, J=4.9 Hz, 1H), 3.81 (s, 3H), 4.48 (s, 2H), 6.81–6.91 (m, 3H), 7.23–7.28 (m, 1H) ppm IR (liquid film); 3502, 2954, 2870, 1489, 1457, 1267, 1080, 1053 cm$^{-1}$ Mass (m/z, %); 280 (M$^+$, 2), 135 (31), 121 (100), 107 (8), 91 (9), 69 (13), 55 (14).

REFERENCE EXAMPLE 2

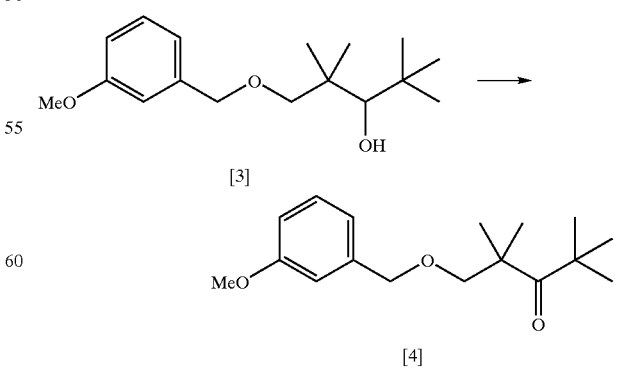

In a nitrogen atmosphere, 9.9 g of celite and 4.61 g (16.5 mmol) of 1-(3-methoxybenzyloxy)-2,2,4,4-tetramethyl-3- pentanol (compound (3)) were added to 75 ml of dichloromethane at room temperature, followed by stirring. To this solution, 4.26 g (19.7 mmol) of PCC was added, followed by stirring for 7 hours. Then, 800 mg (3.71 mmol) of PCC was further added, followed by stirring overnight. To the reaction mixture, diethyl ether was added, followed by filtration with celite. The filtrate was concentrated, subjected to a silica gel column and eluted with a 10:1 mixed solvent of hexane and ethyl acetate, to obtain 4.32 g of 1-(3-methoxybenzyloxy)-2,2,4,4-tetramethyl-3-pentane (compound (4)) in a yield of 94.4% as a colorless oily substance.

$^1$HNMR (400 MHz, CDCl$_3$); δ 1.23 (s, 9H), 1.28 (s, 6H), 3.50 (s, 2H), 3.80 (s, 3H), 4.47 (s, 2H), 6.78–6.88 (m, 3H), 7.23 (t, J=8.1 Hz, 1H) ppm IR (liquid film); 2959, 2870, 1658, 1480, 1466, 1458, 1267, 1108, 1049 cm$^{-1}$ Mass (m/z, %); 278 (M$^+$, 100), 222 (50), 121 (31), 97 (5), 55 (8).

REFERENCE EXAMPLE 3

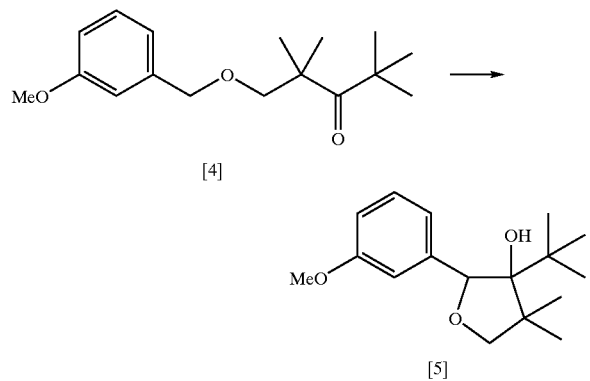

In a nitrogen atmosphere, 1.50 ml (11.4 mmol) of diisopropylamine and 6.60 ml (10.6 mmol) of a 1.6 M butyl lithium hexane solution, were added to 15 ml of anhydrous THF at room temperature, followed by stirring for 30 minutes. To this solution, 1.48 g (5.32 mmol) of 1-(3-methoxybenzyloxy)-2,2,4,4-tetramethyl-3-pentanone (compound (4)) dissolved in 10 ml of THF, was added at −78° C., followed by stirring for 2 hours. The reaction solution was gradually heated to room temperature and stirred for 3 hours and 20 minutes. The reaction mixture was put into a saturated sodium chloride aqueous solution and extracted with ethyl acetate. The extract layer was washed with a saturated sodium chloride aqueous solution, dried over anhydrous magnesium sulfate and then concentrated. The concentrated product was subjected to a silica gel column and eluted with a 1:2 mixed solvent of hexane and ethyl acetate, to obtain 1.30 g of 3-t-butyl-3-hydroxy-2-(3-methoxyphenyl)-4,4-dimethyl-2,3,4,5-tetrahydrofuran (compound (5)) in a yield of 87.8%. Melting point: 83.0–83.5° C. (colorless granular crystals, recrystallized from hexane and ethyl acetate)

$^1$HNMR (400 MHz, CDCl$_3$); δ 0.90 (broad s, 9H), 1.19 (s, 3H), 1.39 (s, 3H), 1.92 (s, 1H), 3.80 (q$_{AB}$, J=8.1 Hz, 2H), 3.80 (s, 3H), 5.00 (s, 1H), 6.80 (dd, J=7.8 and 2.4 Hz, 1H), 7.10 (d, J=2.4 Hz, 1H), 7.11 (d, J=7.8 Hz, 1H), 7.21 (t, J=7.8 Hz, 1H) ppm IR (liquid film); 3493, 2962, 2881, 1591, 1481, 1278, 1070, 1048 cm$^{-1}$ Mass (m/z, %); 278 (M$^+$, 1), 260 (29), 245 (100), 203 (12), 189 (45), 135 (52), 121 (10), 107 (11), 77 (9), 55 (33).

REFERENCE EXAMPLE 4

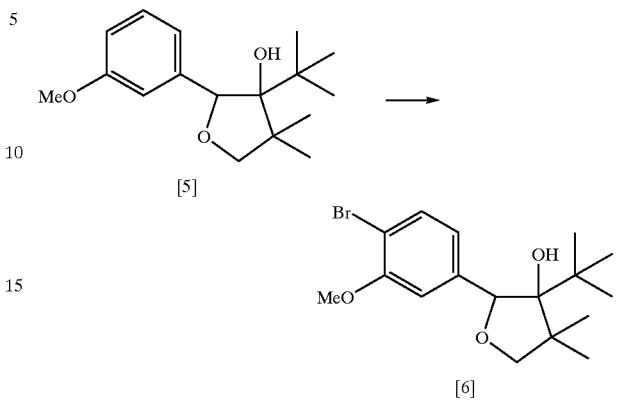

2.16 g (7.77 mmol) of 3-t-butyl-3-hydroxy-2-(3-methoxyphenyl)-4,4-dimethyl-2,3,4,5-tetrahydrofuran (compound (5)) was added to a mixed solvent of 20 ml of THF and 2 ml of H$_2$O, followed by stirring at 0° C. To this solution, 1.54 g (8.65 mmol) of NBS was added, and while gradually raising the temperature to room temperature, stirring was continued overnight. Then, 140 mg (0.787 mmol) of NBS was further added, followed by stirring for 6 hours. The reaction mixture was put into a saturated sodium chloride aqueous solution and extracted with ethyl acetate. The extract layer was washed sequentially with an aqueous sodium thiosulfate solution and a saturated sodium chloride aqueous solution, dried over anhydrous magnesium sulfate and then concentrated. The concentrated product was crystallized from a mixed solvent of ethyl acetate and hexane to obtain 1.323 g of 2-(4-bromo-3-methoxyphenyl)-3-t-butyl-3-hydroxy-4,4-dimethyl-2,3,4,5-tetrahydrofuran (compound (6)) in a yield of 47.7%.

$^1$HNMR (400 MHz, CDCl$_3$); δ 0.89 (s, 9H), 1.20 (s, 3H), 1.38 (s, 3H), 1.92 (s, 1H), 3.80 (q$_{AB}$, J=8.3 Hz, 2H), 3.89 (s, 3H), 4.98 (s, 1H), 7.02 (dd, J=8.1 and 2.0 Hz, 1H), 7.12 (d, J=2.0 Hz, 1H), 7.45 (d, J=8.1 Hz, 1H) ppm Mass (m/z, %); 358 (M$^+$+2, 2.4), 356 (M$^+$, 2.5), 340 (19), 338 (20), 325 (79), 323 (84), 215 (73), 213 (67), 201 (18), 199 (19), 109 (10), 55 (100).

REFERENCE EXAMPLE 5

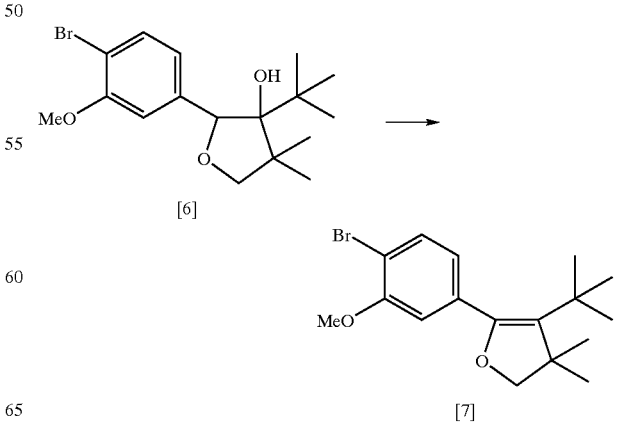

4.68 g (13 mmol) of 4-t-butyl-5-(4-bromo-3-methoxyphenyl)-4-hydroxy-3,3-dimethyl-2,3,4,5-tetrahydrofuran (compound (6)) was added to 30 ml of anhydrous toluene at room temperature in a nitrogen atmosphere, followed by stirring for 10 minutes. To this reaction solution, 0.27 g (1.4 mmol, 0.1 equivalent) of p-toluenesulfonic acid monohydrate was added, followed by stirring at 120° C. for 30 minutes. The reaction solution was returned to room temperature, and this solution was put into a mixed solution of ethyl acetate and a saturated sodium chloride aqueous solution to carry out extraction. The obtained organic layer was washed with a saturated sodium chloride aqueous solution. This organic layer was dried over anhydrous magnesium sulfate and concentrated. The concentrated product was subjected to a silica gel column and eluted with a 2:1 mixed solvent of hexane and ethyl acetate to obtain 3.78 g (11.2 mmol) of 4-t-butyl-5-(4-bromo-3-methoxyphenyl)-3,3-dimethyl-2,3-dihydrofuran (compound (7)) in a yield of 85% as a colorless oily substance.

$^1$HNMR (400 MHz, CDCl$_3$); δ 1.06 (s, 9H), 1.33 (s, 6H), 3.87 (s, 2H), 3.9 (s, 3H), 6.79 (dd, J=7.9 and 1.6 Hz, 1H), 6.82 (d, J=1.6 Hz, 1H), 7.49 (d, J=7.9 Hz, 1H) ppm IR (liquid film); 2957, 2866, 1739, 1650, 1570, 1480, 1392, 1237, 1049, 1025, 795 cm$^{-1}$ Mass (m/z, %); 340 (M$^+$+2, 26), 338 (M$^+$, 26), 325 (97), 323 (100), 283 (6), 282 (3), 281 (4), 187 (7), 185 (5), 172 (4), 170 (3), 77 (7), 55 (67).

REFERENCE EXAMPLE 6

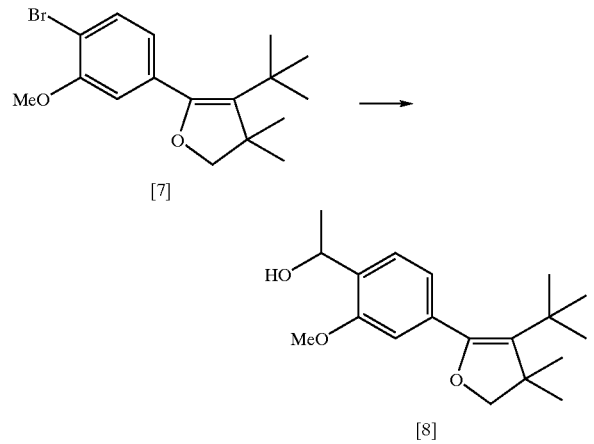

To a solution having 5.05 g (14.88 mmol) of 4-t-butyl-5-(4-bromo-3-methoxyphenyl)-3,3-dimethyl-2,3-dihydrofuran (compound (7)) dissolved in THF (50 ml) at room temperature in a nitrogen atmosphere, a 1.63 M butyl lithium hexane solution (10.5 ml, 17.1 mmol) was added at −78° C., followed by stirring for 15 minutes. Then, acetaldehyde (14.0 ml, 45.1 mmol) dissolved in hexane, was added thereto, followed by stirring for 30 minutes. To this reaction solution, a small amount of H$_2$O was dropwise added to terminate the reaction, and the reaction solution was put into a saturated ammonium chloride aqueous solution (100 ml) and extracted with ethyl acetate (100 ml). The aqueous layer was extracted again with ethyl acetate (100 ml), and the extract was put together with the previous organic layer, followed by washing with a saturated sodium chloride aqueous solution (200 ml×3). The organic layer was dried over anhydrous magnesium sulfate and concentrated, and the residue was obtained as a slightly yellow oily substance (4.93 g). This residue was subjected to silica gel column and eluted with a 4:1 mixed solvent of hexane and ethyl acetate to obtain the desired 4-t-butyl-5-[4-(1-hydroxyethyl)-3-methoxyphenyl]-3,3-dimethyl-2,3-dihydrofuran (compound (8)) as a colorless solid (3.73 g, 12.25 mmol, 82.3%).

$^1$HNMR (400 MHz, CDCl$_3$); δ 1.06 (s, 9H), 1.34 (s, 6H), 1.49 (d, J=6.2 Hz, 3H), 2.60 (d, J=4.9 Hz, 1H), 3.87 (s, 3H), 3.87 (s, 2H), 5.08 (pent, J=6.2 Hz, 1H), 6.79 (s, 1H), 6.90 (d, J=7.6 Hz, 1H), 7.28 (d, J=7.6 Hz, 1H) ppm $^{13}$CNMR (125 MHz, CDCl$_3$); δ 22.9, 27.4, 32.4, 32.5, 47.1, 66.3, 83.0, 111.9, 122.5, 125.5, 125.6, 133.3, 136.2, 149.8, 156.0 ppm IR (KBr); 3491, 2962, 2870, 1651, 1604, 1461, 1402, 1229, 1129, 1088, 859 cm$^{-1}$ Mass (m/z, %); 304 (M$^+$, 5), 303 (9), 287 (19), 271 (100), 177 (14), 161 (69), 149 (10), 135 (11), 111 (23), 55 (88).

REFERENCE EXAMPLE 7

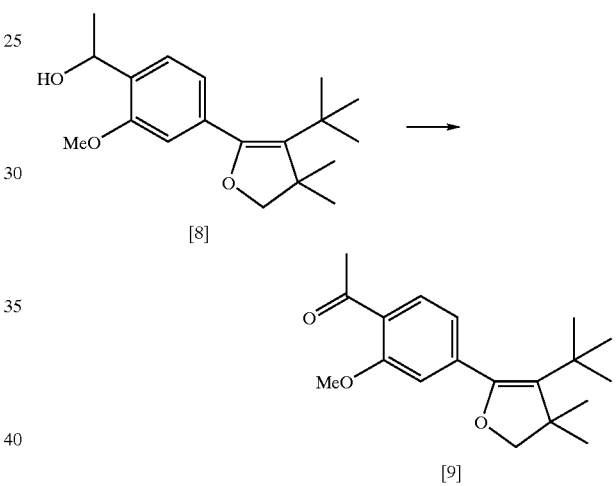

To a solution having 4-t-butyl-5-[4-(1-hydroxyethyl)-3-methoxyphenyl]-3,3-dimethyl-2,3-dihydrofuran (compound (8)) (1.02 g, 3.351 mmol) dissolved in DMSO (10 ml) and THF (5 ml) at room temperature in a nitrogen atmosphere, triethylamine (1.65 ml, 11.8 mmol) and a pyridine/sulfur trioxide complex (1.60 g, 10.1 mmol) was added, followed by stirring for 1 hour. This reaction solution was put into a saturated sodium chloride aqueous solution (50 ml) and extracted with ethyl acetate (50 ml). The aqueous layer was extracted again with ethyl acetate (50 ml), and the extract was put together with the previous organic layer, followed by washing with a saturated sodium chloride aqueous solution (100 ml×3). The organic layer was dried over anhydrous magnesium sulfate and concentrated, and the residue was obtained as a slightly yellow oily substance (1.02 g). This residue was subjected to a silica gel column and eluted with a 4:1 mixed solvent of hexane and ethyl acetate to obtain the desired 5-(4-acetyl-3-methoxyphenyl)-4-t-butyl-3,3-dimethyl-2,3-dihydrofuran (compound (9)) as a colorless solid (943 mg, 3.118 mmol, 93.0%).

$^1$HNMR (400 MHz, CDCl$_3$); δ 1.07 (s, 9H), 1.34 (s, 6H), 2.61 (s, 3H), 3.89 (s, 2H), 3.92 (s, 3H), 6.89 (d, J=1.3 Hz, 1H), 6.95 (dd, J=7.8 and 1.3 Hz, 1H), 7.70 (d, J=7.8 Hz, 1H) ppm $^{13}$CNMR (100 MHz, CDCl$_3$); δ 27.3, 31.8, 32.4, 32.4, 47.3, 55.5, 83.8, 113.1, 122.4, 126.4, 127.7, 129.9, 141.8, 148.8, 158.4, 199.4 ppm IR (KBr): 2957, 2868, 1676, 1600, 1560, 1463, 1401, 1232, 1053 cm$^{-1}$ Mass (m/z, %); 302 (M$^+$, 27), 287 (100), 231 (40), 203 (14), 177 (78), 149 (9), 135 (6), 55 (48).

REFERENCE EXAMPLE 8

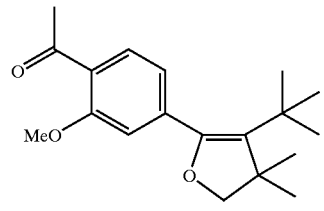

[9]

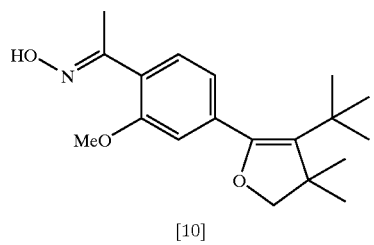

[10]

To a solution having 5-(4-acetyl-3-methoxyphenyl)-4-t-butyl-3,3-dimethyl-2,3-dihydrofuran (compound (9)) (1.35 g, 4.464 mmol) dissolved in ethanol (15 ml) at room temperature, sodium hydrogencarbonate (562 mg, 6.69 mmol) was added, and then hydroxylamine hydrochloride (472 mg, 6.79 mmol) was added, followed by refluxing at 90° C. for 30 minutes. This reaction solution was put into a saturated sodium chloride aqueous solution (50 ml) and extracted with ethyl acetate (50 ml). The aqueous layer was extracted again with ethyl acetate (50 ml), and the extract was put together with the previous organic layer, followed by washing with a saturated sodium chloride aqueous solution (100 ml×3). The organic layer was dried over anhydrous magnesium sulfate and concentrated, and the residue was obtained as a slightly yellow solid (1.38 g). The residue was subjected to a silica gel column and eluted with a 4:1 mixed solvent of hexane and ethyl acetate to obtain the desired 4-t-butyl-5-[4-(1-hydroxyiminoethyl)-3-methoxyphenyl]-3,3-dimethyl-2,3-dihydrofuran (compound (10)) as a colorless solid (1.11 g, 3.497 mmol, 78.3%).

$^1$HNMR (400 MHz, CDCl$_3$); δ 1.07 (s, 9H), 1.34 (s, 6H), 2.22 (s, 3H), 3.84 (s, 3H), 3.88 (s, 2H), 6.83 (d, J=1.4 Hz, 1H), 6.90 (dd, J=7.6 and 1.4 Hz, 1H), 7.23–7.27 (m, 1H), 7.81 (br-s, 1H) ppm $^{13}$CNMR (125 MHz, CDCl$_3$); δ 15.1, 27.4, 32.4, 32.5, 47.2, 55.5, 83.1, 112.6, 122.3, 125.9, 126.4, 128.8, 138.1, 149.5, 156.5, 156.9 ppm IR (KBr); 3228, 2963, 2865, 1602, 1561, 1396, 1311, 1226, 1051, 930 cm$^{-1}$ Mass (m/z, %); 317 (M$^+$, 29), 302 (100), 286 (32), 270 (13), 260 (10), 246 (18), 230 (11), 214 (14), 192 (14), 176 (7), 57 (4).

REFERENCE EXAMPLE 9

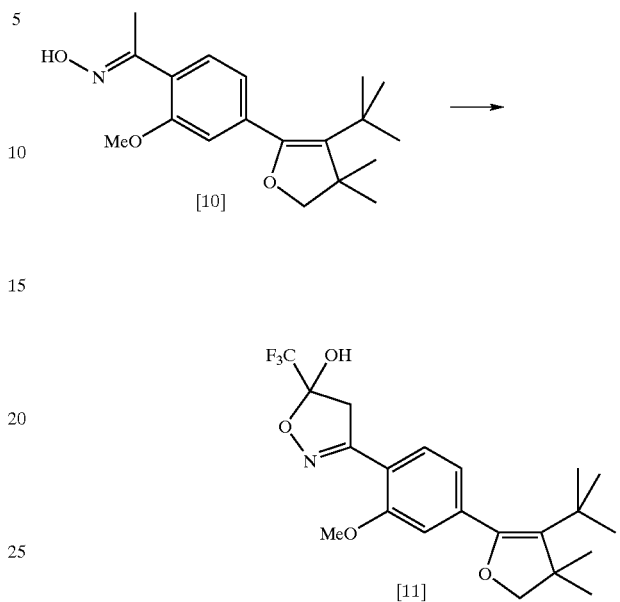

To a solution having 4-t-butyl-5-[4-(1-hydroxyiminoethyl)-3-methoxyphenyl]-3,3-dimethyl-2,3-dihydrofuran (compound (10)) (980 mg, 3.087 mmol) dissolved in THF (10 ml) at room temperature in a nitrogen atmosphere, 1.61 M butyl lithium hexane solution (4.20 ml, 6.76 mmol) was added at −78° C., followed by stirring for 5 minutes. Trifluoroacetic acid S-ethyl ester (0.50 ml, 8.90 mmol) was added thereto, and the mixture was gradually returned to room temperature and stirred for 1 day. This reaction solution was put into a saturated ammonium chloride aqueous solution (50 ml) and extracted with ethyl acetate (50 ml). The aqueous layer was extracted again with ethyl acetate (50 ml), and the extract was put together with the previous organic layer, followed by washing with a saturated sodium chloride aqueous solution (100 ml×3). The organic layer was dried over anhydrous magnesium sulfate and concentrated, and the residue was obtained as a slightly yellow oily substance (1.25 mg). This residue was subjected to a silica gel column and eluted with a 4:1 mixed solvent of hexane and ethyl acetate to obtain the desired 4-t-butyl-5-[4-(5-trifluoromehtyl-5-hydroxyisoxazolin-3-yl)-3-methoxyphenyl]-3,3-dimethyl-2,3-dihydrofuran (compound (11)) as a colorless solid (841 mg, 2.034 mmol, 65.9%).

$^1$HNMR (400 MHz, CDCl$_3$); δ 1.07 (s, 9H), 1.34 (s, 6H), 3.49 (br-s, 1H), 3.63 (d, J=18.8 Hz, 1H), 3.84 (d, J=18.8 Hz, 1H), 3.88 (s, 3H), 3.89 (s, 2H), 6.86 (d, J=1.4 Hz, 1H), 6.96 (dd, J=8.0 and 1.4 Hz, 1H), 7.77 (d, J=8.0 Hz, 1H) ppm $^{13}$CNMR (100 MHz, CDCl$_3$); δ 27.3, 32.5, 32.5, 45.4, 47.3, 55.6, 83.1, 103.1 (q, J=33.7 Hz), 113.0, 116.4, 122.0 (d, J=283.3 Hz), 122.8, 126.7, 128.7, 140.1, 148.5, 155.7, 157.0 ppm IR (KBr); 3329, 2962, 2873, 1605, 1466, 1410, 1185, 1050, 1005, 860 cm$^{-1}$ Mass (m/z, %); 413 (M$^+$, 29), 398 (100), 380 (28), 342 (26), 324 (12), 288 (35), 270 (60), 214 (22), 160 (22), 57 (8).

REFERENCE EXAMPLE 10

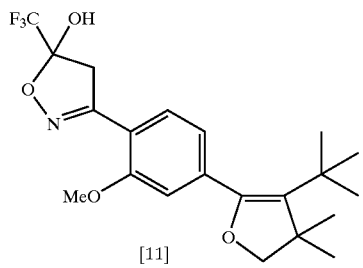

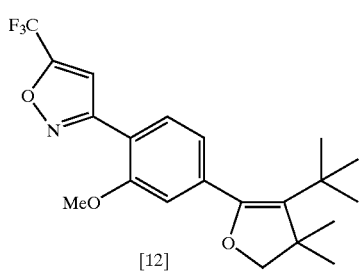

To a solution having 4-t-butyl-5-[4-(5-trifluoromethyl-5-hydroxyisoxazolin-3-yl)-3-methoxyphenyl]-3,3-dimethyl-2,3-dihydrofuran (compound (11)) (922 mg, 2.230 mmol) dissolved in toluene (10 ml) at room temperature, p-toluenesulfonic acid monohydrate (45.8 mg, 0.241 mmol) was added, followed by refluxing at 130° C. for 1 hour. This reaction solution was put into a saturated sodium hydrogencarbonate solution (50 ml) and extracted with ethyl acetate (50 ml). The aqueous layer was extracted again with ethyl acetate (50 ml), and the extract was put together with the previous organic layer, followed by washing with a saturated sodium chloride aqueous solution (100 ml×3). The organic layer was dried over anhydrous magnesium sulfate and concentrated, and the residue was obtained as a slightly yellow solid (930 mg). This residue was subjected to a silica gel column and eluted with a 4:1 mixed solvent of hexane and ethyl acetate to obtain the desired 4-t-butyl-5-[4-(5-trifluoromethyl-3-isoxazolyl)-3-methoxyphenyl]-3,3-dimethyl-2,3-dihydrofuran (compound (12)) as a colorless solid (748 mg, 1.983 mmol, 88.9%).

$^1$HNMR (400 MHz, CDCl$_3$); δ 1.09 (s, 9H), 1.36 (s, 6H), 3.90 (s, 2H), 3.93 (s, 3H), 6.95 (d, J=1.2 Hz, 1H), 7.02 (dd, J=7.8 and 1.2 Hz, 1H), 7.23 (d, J=0.7 Hz, 1H), 7.89 (d, J=7.8 Hz, 1H) ppm $^{13}$CNMR (100 MHz, CDCl$_3$); δ 27.4, 32.5, 32.5, 47.3, 55.7, 83.6, 106.8 (d, J=1.7 Hz), 113.0, 115.8, 118.0 (d, J=269.8 Hz), 122.9, 126.4, 128.8, 140.2, 148.8, 156.6, 157.8 (q, J=42.0 Hz), 159.8 ppm IR (KBr); 2961, 2870, 1606, 1450, 1313, 1178, 1152, 1052, 967, 834 cm$^{-1}$ Mass (m/z, %); 395 (M$^+$, 22), 380 (100), 345 (16), 338 (19), 324 (25), 270 (53), 244 (10), 228 (7), 214 (9), 160 (13), 149 (10), 57 (15).

REFERENCE EXAMPLE 11

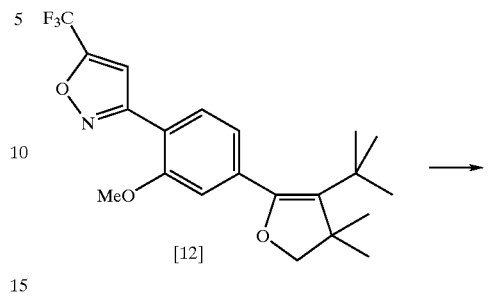

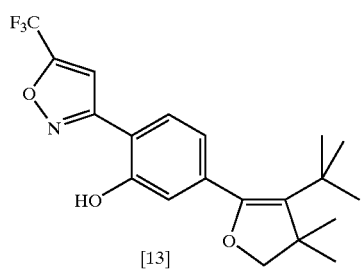

Ethanethiol (0.40 ml, 5.40 mmol) was added to DMF (3 ml) having 135 mg (3.38 mmol) of 60% sodium hydride suspended at 0° C. in a nitrogen atmosphere, followed by stirring for 15 minutes. To this reaction solution, a solution having 4-t-butyl-5-[4-(5-trifluoromethyl-3-isoxazolyl)-3-methoxyphenyl]-3,3-dimethyl-2,3-dihydrofuran (compound (12)) (664 mg, 1.679 mmol) dissolved in DMF (3 ml), was dropwise added, followed by heating at 140° C. for 1 hours. This reaction solution was put into a saturated ammonium chloride aqueous solution (50 ml) and extracted with ethyl acetate (50 ml). The aqueous layer was extracted again with ethyl acetate, and the extract was put together with the previous organic layer, followed by washing with a saturated sodium chloride aqueous solution (100 ml×3). The organic layer was dried over anhydrous magnesium sulfate and concentrated, and the residue was obtained as a slightly yellow solid (671 mg). This residue was subjected to a silica gel column and eluted with a 4:1 mixed solvent of hexane and ethyl acetate to obtain the desired 4-t-butyl-5-[4-(5-trifluoromethyl-3-isoxazolyl)-3-hydroxyphenyl]-3,3-dimethyl-2,3-dihydrofuran (compound (13)) as a colorless solid (533 mg, 1.398 mmol, 83.3%).

$^1$HNMR (400 MHz, CDCl$_3$); δ 1.08 (s, 9H), 1.34 (s, 6H), 3.89 (s, 2H), 6.95 (dd, J=8.1 and 1.5 Hz, 1H), 7.06 (d, J=1.2 Hz, 1H), 7.57 (d, J=1.5 Hz, 1H), 7.84 (d, J=8.1 Hz, 1H), 10.6 (s, 1H) ppm $^{13}$CNMR (100 MHz, CDCl$_3$); δ 27.3, 32.5, 32.5, 47.4, 83.3, 109.2, 118.7 (q, J=266.8 Hz), 119.1, 121.6, 126.0, 127.5 (d, J=3.3 Hz), 138.4 (q, J=44.5 Hz), 142.1, 148.4, 157.3, 163.0 ppm IR (KBr); 3355, 3148, 2960, 2868, 1629, 1576, 1494, 1330, 1179, 1147, 1052, 765 cm$^{-1}$ Mass (m/z, %); 381 (M$^+$, 61), 366 (100), 324 (6), 310 (88), 278 (11), 256 (85), 228 (18), 200 (17), 57 (19).

REFERENCE EXAMPLE 12

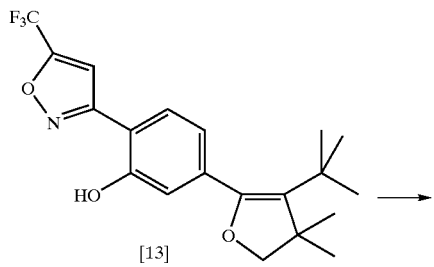

In a nitrogen atmosphere, 1.84 ml (22.8 mmol) of pyridine was added to 30 ml of dichloromethane at 0° C., and further, 1.33 ml (14.3 mmol) of phosphorus oxychloride was added, followed by stirring for 15 minutes. To this reaction solution, a solution having 4-t-butyl-5-[4-(5-trifluoromethyl-3-isoxazolyl)-3-hydroxyphenyl]-3,3-dimethyl-2,3-dihydrofuran (compound 13)) (1.44 g, 3.78 mmol) dissolved in dichloromethane (12 ml), was dropwise added, followed by stirring at 0° C. for 2 hours. Further, the reaction solution was gradually returned to room temperature and stirred for 1 day. The reaction solution was again cooled to 0° C., and 3.68 ml (45.5 mmol) of pyridine was added. Further, 3.20 ml (47.3 mmol) of ethylene cyanohydrin was added, and the mixture was gradually returned to room temperature and stirred for 1 day. The reaction solution was put into pure water (50 ml) and extracted with ethyl acetate (50 ml). The aqueous layer was again extracted with ethyl acetate (50 ml), and the extract was put together with the previous organic layer, followed by washing with pure water (100 ml×3). The organic layer was dried over anhydrous magnesium sulfate and concentrated to obtain the desired phosphoric acid 5-(3-t-butyl-4,4-dimethyl-4,5-dihydrofuran-2-yl)-2-(5-trifluoromethylisoxazol-3-yl)phenylester bis-(2-cyanoethyl)ester (compound (15)) as a slightly yellow oily substance (2.10 g, 3.70 mmol, 98.1%).

$^1$HNMR (500 MHz, $CDCl_3$); δ 1.08 (s, 9H), 1.35 (s, 6H), 2.80 (m, 4H), 3.90 (s, 2H), 4.45 (m, 4H), 7.33 (dd, 1H), 7.53 (d, 1H), 7.63 (d, 1H), 8.09 (dd, 1H), ppm

REFERENCE EXAMPLE 13

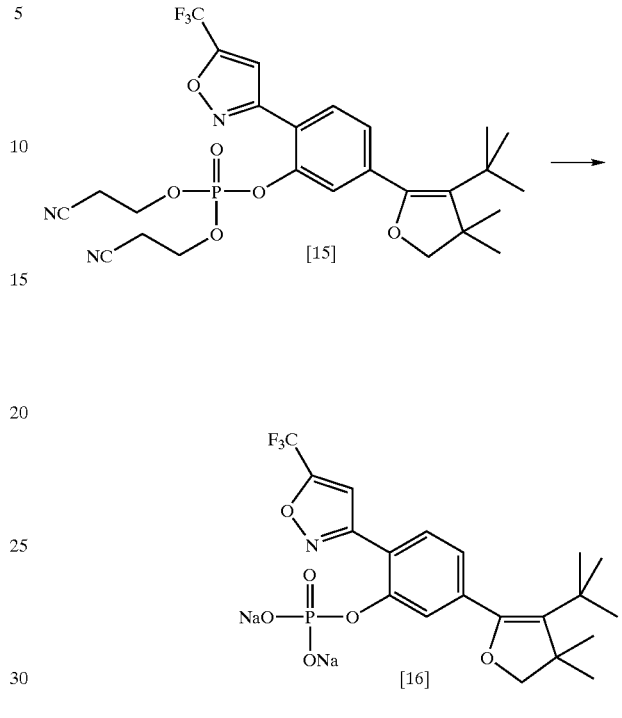

At room temperature, a 28% sodium methylate methanol solution (1.6 ml) was added to a solution having phosphoric acid-5-(3-t-butyl-4,4-dimethyl-4,5-dihydrofuran-2-yl)-2-(5-trifluoromethylisoxazol-3-yl)phenylester bis-(2-cyanoethyl)ester (compound (15)) (1.20 g, 2.11 mmol) dissolved in methanol (40 ml), followed by stirring for 1 hour and 30 minutes. To this reaction solution, a saturated sodium hydrogencarbonate aqueous solution (2.0 ml) was added and further stirred for 30 minutes and then concentrated to obtain a white solid. To this solid, methanol (20 ml) was added, and insolubles were removed by filtration. The filtrate was concentrated to obtain the desired phosphoric acid mono-[5-(3-t-butyl-4,4-dimethyl-4,5-dihydrofuran-2-yl)-2-(5-trifluoromethylisoxazol-3-yl)phenyl]ester disodium salt (compound (16)) as a white solid (0.69 g, 1.37 mmol, 64.5%).

$^1$HNMR (500 MHz, $CD_3OD$); δ 1.11 (s, 9H), 1.34 (s, 6H), 3.83 (s, 2H), 6.98 (dd, 1H), 7.78 (d, 1H), 7.85 (d, 1H), 8.05 (d, 1H), ppm

EXAMPLE 1

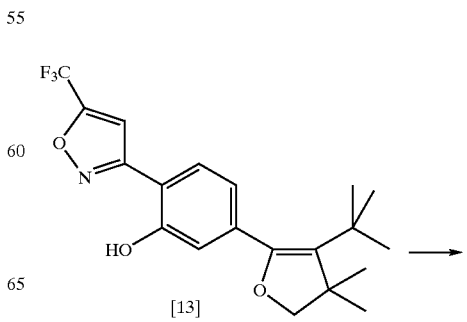

-continued

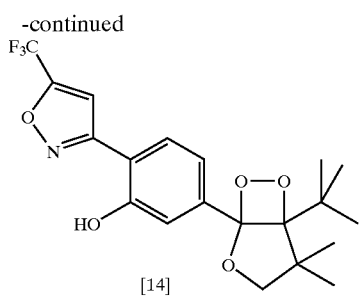

[14]

To a solution having 4-t-butyl-5-[4-(5-trifluoromethyl-3-isoxazolyl)-3-hydroxyphenyl]-3,3-dimethyl-2,3-dihydrofuran (compound (13)) (80.0 mg, 0.2098 mmol) dissolved in CH$_2$Cl$_2$ (5 ml) at 0° C. in an oxygen atmosphere, TPP (2.1 mg) was added, and then irradiation by a sodium lamp was carried out, followed by stirring for 30 minutes. This reaction solution was concentrated, and the residue was obtained as a green solid (81.2 mg). This residue was subjected to a silica gel column and eluted with a 20:1 mixed solvent of hexane and diethyl ether to obtain the desired 4-t-butyl-5-[4-(5-trifluoromethyl-3-isoxazolyl)-3-hydroxyphenyl]-4,4-dimethyl-2,6,7-trioxabicyclo[3.2.0]heptane (compound (14)) as a slightly yellow solid (75.3 mg, 0.1822 mmol, 86.8%).

$^1$HNMR (400 MHz, CDCl$_3$); δ 1.02 (s, 9H), 1.17 (s, 3H), 1.39 (s, 3H), 3.85 (d, J=8.3 Hz, 1H), 4.60 (d, J=8.3 Hz, 1H), 7.28 (dd, J=8.3 and 1.5 Hz, 1H), 7.39 (d, J=1.5 Hz, 1H), 7.59 (d, J=1.5 Hz, 1H), 7.91 (d, J=8.3 Hz, 1H), 10.67 (s, 1H) ppm $^{13}$CNMR (100 MHz, CDCl$_3$); δ 18.5, 25.1, 27.0, 36.8, 45.7, 80.5, 105.4, 110.3, 115.9, 117.9, 118.7 (q, J=267.0 Hz), 119.7, 126.0, 127.5 (d, J=2.5 Hz), 138.7 (q, J=44.5 Hz), 141.8, 157.3, 162.7 ppm IR (KBr); 3144, 2975, 2898, 1613, 1550, 1494, 1371, 1331, 1219, 1149, 1035, 959, 872 cm$^{-1}$ Mass (m/z, %); 413 (M$^+$, 1), 381 (13), 366 (20), 357 (28), 328 (7), 273 (33), 256 (100), 228 (13), 200 (14), 57 (25)

EXAMPLE 2

1 ml of a 1.00×10$^{-5}$M acetonitrile solution of 4-t-butyl-5-[4-(5-trifluoromethyl-3-isoxazolyl)-3-hydroxyphenyl]-4,4-dimethyl-2,6,7-trioxabicyclo[3.2.0]heptane (compound (14)) obtained in Example 1, was added at 40° C. to 2 ml of a 1.00×10$^{-2}$M DMSO solution of tetrabutylammonium fluoride. The luminescence at that time was measured by a fluorescence analyzer. The luminous quantum yield at that time was estimated to be 0.44, the half value period of luminescence was 1,400 seconds, and λ$_{max}$ was 481 nm.

EXAMPLE 3

1 ml of a 1.00×10$^{-4}$M acetonitrile solution of 4-t-butyl-5-[4-(5-trifluoromethyl-3-isoxazolyl)-3-hydroxyphenyl]-4,4-dimethyl-2,6,7-trioxabicyclo[3.2.0]heptane (compound (14)) obtained in Example 1, was added at 40° C. to 2 ml of a 0.1N solution of sodium hydroxide. The luminescence at that time was measured by a fluorescent analyzer. The luminous quantum yield at that time was estimated to be 0.39, the half value period of luminescence was 2,700 seconds, and λ$_{max}$ was 479 nm.

EXAMPLE 4

0.1 ml of a 1.00×10$^{-3}$M acetonitrile solution of 4-t-butyl-5-[4-(5-trifluoromethyl-3-isoxazolyl)-3-hydroxyphenyl]-4,4-dimethyl-2,6,7-trioxabicyclo[3.2.0]heptane (compound (14)) obtained in Example 1, was added at 40° C. to 2 ml of a 0.1N solution of sodium hydroxide+0.9 ml of distilled water. The luminescence at that time was measured by a fluorescent analyzer. The luminous quantum yield at that time was estimated to be 0.24, the half value period of luminescence was 1,200 seconds, and λ$_{max}$ was 476 nm.

EXAMPLE 5

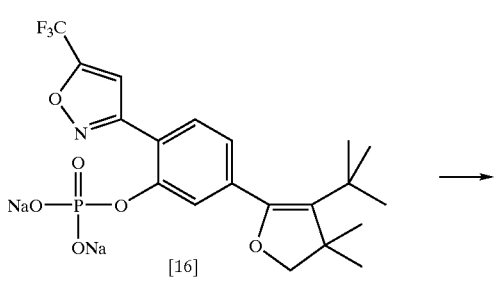

[16]

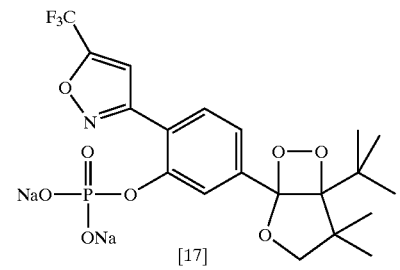

[17]

In an oxygen atmosphere at 0° C., TPP (2.0 mg) was added to a mixed solution having phosphoric acid mono-[5-(3-t-butyl-4,4-dimethyl-4,5-dihydrofuran-2-yl)-2-( 5-trifluoromethylisoxazol-3-yl)phenyl]ester disodium salt (compound (16)) (65.0 mg, 0.129 mmol) dissolved in methanol (4 ml) and dichloromethane (15 ml), followed by stirring for 2 hours under irradiation by a sodium lamp. The reaction mixture was concentrated, and methanol was added to the concentrate, whereupon insolubles were filtered off by means of a 0.45 μm polytetrafluoroethylene filter, followed by concentration again. The concentrate was dissolved in pure water (1.5 ml) and subjected to HPLC employing a polymer type reversed phase C18 fractionation column, and the fraction eluted with water and acetonitrile was subjected to freeze drying to obtain the desired phosphoric acid mono-[5-(5-t-butyl-4,4-dimethyl-2,6,7-trioxabicyclo[3.2.0]hept-1-yl)-2-(5-trifluoromethylisoxazol-3-yl)phenyl]ester disodium salt (compound (17)) as a white solid (52.0 mg, 0.097 mmol, 75.3%).

$^1$HNMR (500 MHz, CD$_3$OD); δ 1.04 (s, 9H), 1.14 (s, 3H), 1.44 (s, 3H), 3.83 (d, 1H), 4.49 (d, 1H), 7.33 (dd, 1H), 7.79 (d, 1H), 7.91 (dd, 1H), 8.35 (d, 1H) ppm The 1,2-dioxetane derivative (1) of the present invention is capable of exhibiting stable luminescence having a high quantum yield and is a stable compound having high thermal stability such that depending upon the cold storage, no decomposition product will be observed upon expiration of one year. Accordingly, measurement of the luminescence can be carried out simply and efficiently, and thus, it is useful, for example, in the field of clinical tests. Further, the 1,2-dioxetane derivative (I) of the present invention not only has both high thermal stability and high luminous efficiency, but also makes it possible to omit an enhancer itself or an operation to add an enhancer in a protic solvent, whereby costs and time can be saved.

The entire disclosure of Japanese Patent Application No. 2001-65347 filed on Mar. 8, 2001 including specification, claims and summary are incorporated herein by reference in its entirety

What is claimed is:

1. A 1,2-dioxetane derivative of the formula (I):

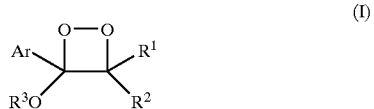

(I)

wherein each of $R^1$ and $R^2$ which are independent of each other, is a hydrogen atom, an alkyl group or an aryl group, or $R^1$ and $R^2$ may together form a cyclic or polycyclic organic ring group spiro-bonded to the dioxetane ring, $R^3$ is an alkyl group or an aryl group, or $R^3$ and $R^1$ or $R^2$ may together form a condensed ring containing the dioxetane ring and a hetero atom, and Ar is a group of the formula (A):

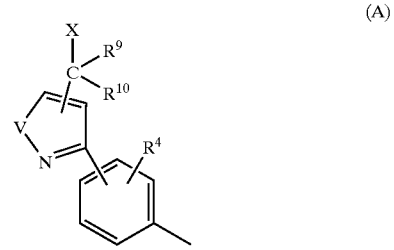

(A)

wherein $R^4$ is a hydroxyl group, an alkoxyl group, an aralkyloxy group, a group of —OSi($R^5R^6R^7$) (wherein each of $R^5$, $R^6$ and $R^7$ which are independent of one another, is an alkyl group or an aryl group), a phosphate group or a group of —S(C=O)$R^8$ (wherein $R^8$ is an alkyl group or an aryl group), each of $R^9$ and $R^{10}$ which are independent of each other, is a hydrogen atom, an alkyl group, an aryl group or a halogen atom, X is a halogen atom, and V is an oxygen atom or a sulfur atom, or wherein Ar is a group of the formula (B):

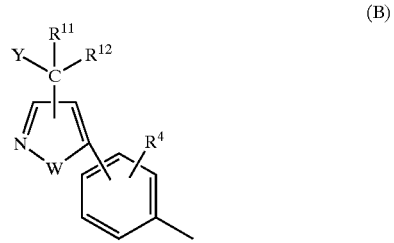

(B)

wherein $R^4$ is the same as $R^4$ in the above formula (A), each of $R^{11}$ and $R^{12}$ which are independent of each other, is a hydrogen atom, an alkyl group, an aryl group or a halogen atom, Y is a halogen atom, and W is an oxygen atom or a sulfur atom.

2. The 1,2-dioxetane derivative according to claim 1, wherein Ar is a group of the formula (a):

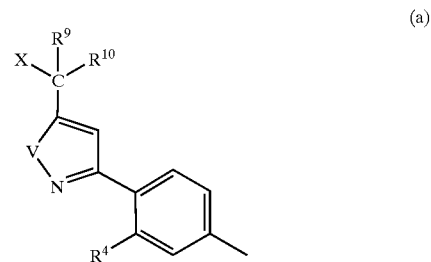

(a)

wherein $R^4$, $R^9$, $R^{10}$, X and V are the same as $R^4$, $R^9$, $R^{10}$, X and V in the above formula (A), or a group of the formula (b):

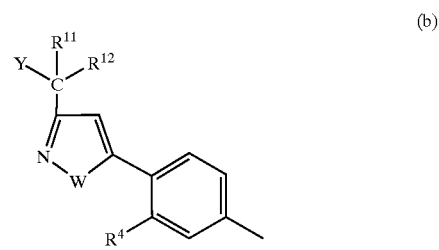

(b)

wherein $R^4$, $R^{11}$, $R^{12}$, Y and W are the same as $R^4$, $R^{11}$, $R^{12}$, Y and W in the above formula (B).

3. The 1,2-dioxetane derivative according to claim 1, wherein $R^3$ and $R^1$ or $R^2$ together form a condensed ring of a dioxetane ring and a furan ring, and $R^2$ or $R^1$ which does not form the condensed ring, is a $C_{3-4}$ alkyl group.

4. The 1,2-dioxetane derivative according to claim 1, which is represented by the formula (I'):

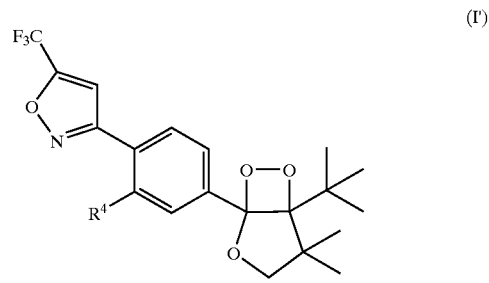

(I')

wherein $R^4$ is the same as $R^4$ in the above formula (A).

5. A chemiluminescent reagent which contains the 1,2-dioxetane derivative as defined in claim 1.

6. A luminescence method which comprises decomposing the 1,2-dioxetane derivative as defined in claim 1 to have chemiluminescence generated.

7. The method according to claim 6, wherein the chemiluminescence is generated in the absence of any other enhancer.

8. A measuring method which comprises measuring hormones, alpha-fetoprotein (AFP), carcinoembryonic antigen (CEA), viral antigens and antibodies, and nucleic acids in a test sample, by means of the luminescence method as defined in claim 6.

9. A luminescence method which comprises the emission of light from the 1,2-dioxetane derivative as defined in claim 1 in a protic solvent in the absence of any other enhancer.

10. The method according to claim 9, wherein the luminous quantum yield is at least 1%.

* * * * *